US009835596B2

(12) United States Patent
Guan et al.

(10) Patent No.: US 9,835,596 B2
(45) Date of Patent: Dec. 5, 2017

(54) SYSTEM AND METHOD FOR IDENTIFICATION, GROUPING AND SIZING OF EMBEDDED FLAWS IN ROTOR COMPONENTS USING ULTRASONIC INSPECTION

(71) Applicants: Xuefei Guan, Princeton, NJ (US); Jingdan Zhang, Bellevue, WA (US); Shaohua Kevin Zhou, Plainsboro, NJ (US); El Mahjoub Rasselkorde, Monroeville, PA (US); Waheed A. Abbasi, Murrysville, PA (US); Steve H. Radke, Orlando, FL (US); Chin-Sheng Lee, Winter Springs, FL (US); Ashley L. Lewis, Oviedo, FL (US)

(72) Inventors: Xuefei Guan, Princeton, NJ (US); Jingdan Zhang, Bellevue, WA (US); Shaohua Kevin Zhou, Plainsboro, NJ (US); El Mahjoub Rasselkorde, Monroeville, PA (US); Waheed A. Abbasi, Murrysville, PA (US); Steve H. Radke, Orlando, FL (US); Chin-Sheng Lee, Winter Springs, FL (US); Ashley L. Lewis, Oviedo, FL (US)

(73) Assignee: Siemens Energy, Inc., Orlando, FL (US)

( * ) Notice: Subject to any disclaimer, the term of this patent is extended or adjusted under 35 U.S.C. 154(b) by 847 days.

(21) Appl. No.: 14/146,751

(22) Filed: Jan. 3, 2014

(65) Prior Publication Data
US 2014/0200853 A1    Jul. 17, 2014

Related U.S. Application Data

(60) Provisional application No. 61/753,620, filed on Jan. 17, 2013.

(51) Int. Cl.
G01N 29/44        (2006.01)
G01N 29/06        (2006.01)
G06T 17/00        (2006.01)

(52) U.S. Cl.
CPC ....... *G01N 29/4445* (2013.01); *G01N 29/069* (2013.01); *G06T 17/00* (2013.01); *G01N 2291/2693* (2013.01)

(58) Field of Classification Search
USPC .................. 702/189; 382/128, 149; 345/420; 128/920
See application file for complete search history.

(56) References Cited

U.S. PATENT DOCUMENTS 3,981,184 A    9/1976  Matay
5,275,052 A    1/1994  O'Maley
(Continued)

FOREIGN PATENT DOCUMENTS

JP    2006275977 A    10/2006

OTHER PUBLICATIONS

PCT International Search Report dated Sep. 2, 2014 corresponding to PCT International Application No. PCT/US2014/010420 filed Jan. 7, 2014 (17 pages).
(Continued)

*Primary Examiner* — Lam Nguyen

(57) ABSTRACT

A method and software system for flaw identification, grouping and sizing for fatigue life assessment for rotors used in turbines and generators. The method includes providing ultrasonic data of a plurality of rotor slices and providing volume reconstruction of the ultrasonic data. The method also includes providing in-slice identification, grouping and sizing of flaw indications in the rotor based on the volume reconstruction. Further, the method includes providing inter-slice identification, grouping and sizing of
(Continued)

the flaw indications based on the in-slice flaw indications and providing flaw location and size information. The method can be used in both phased-array and A-scan inspections.

10 Claims, 12 Drawing Sheets

(56) References Cited

U.S. PATENT DOCUMENTS

| | | | |
|---|---|---|---|
| 6,343,936 B1 * | 2/2002 | Kaufman | G06K 9/209 128/920 |
| 7,272,254 B2 * | 9/2007 | Shankarappa | G06K 9/00 382/149 |
| 2005/0078858 A1 * | 4/2005 | Yao | G06K 9/00201 382/128 |
| 2008/0245150 A1 | 10/2008 | Abe | |
| 2011/0109627 A1 | 5/2011 | Abbasi | |
| 2011/0113885 A1 | 5/2011 | Ikeda | |

OTHER PUBLICATIONS

Visualizing Industrial CT Volume Data for Nondestructive Testing Applications (XP-31173543); Huang, et al. Published in Vis 2003, IEEE Visualization 2003 Proceedings, Annual IEEE Conference on Visualization, Jan. 1, 2003 (pp. 547-554); 2003; US; Jan. 1, 2003.
PCT International Search Report dated Jun. 3, 2014 corresponding to PCT International Application No. PCT/US2014/010420 filed Jan. 7, 2014 (6 pages).

* cited by examiner

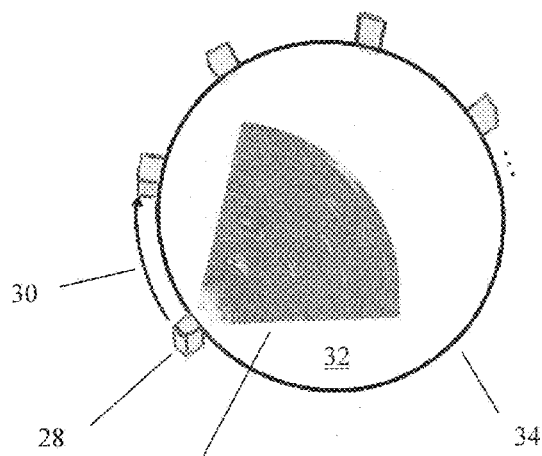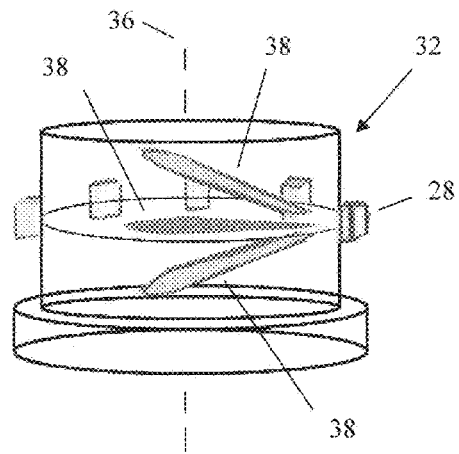
FIGURE 4     FIGURE 5
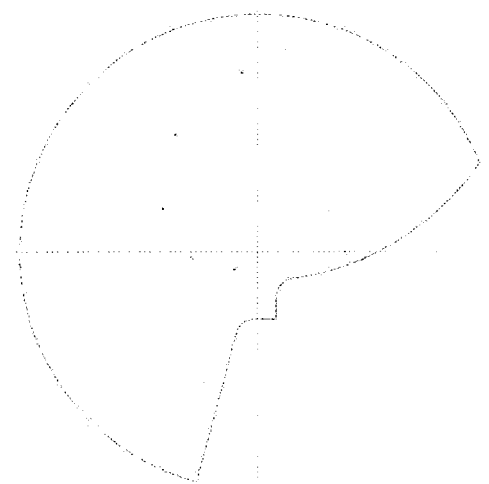
FIGURE 6A     FIGURE 6B

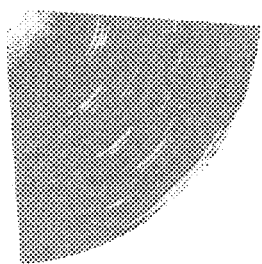
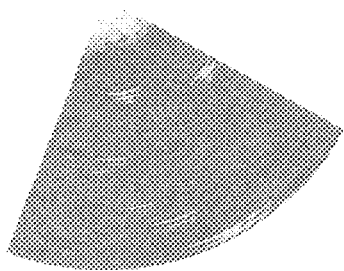
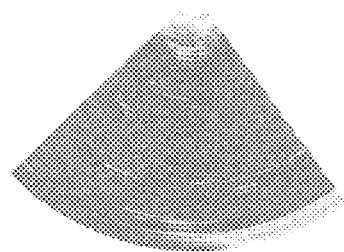
FIGURE 7A    FIGURE 7B    FIGURE 7C
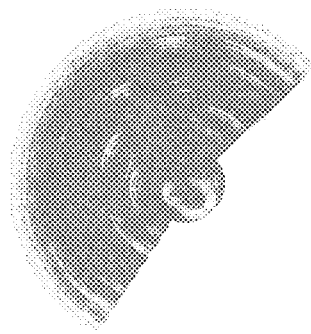
FIGURE 7D    FIGURE 7E    FIGURE 7F

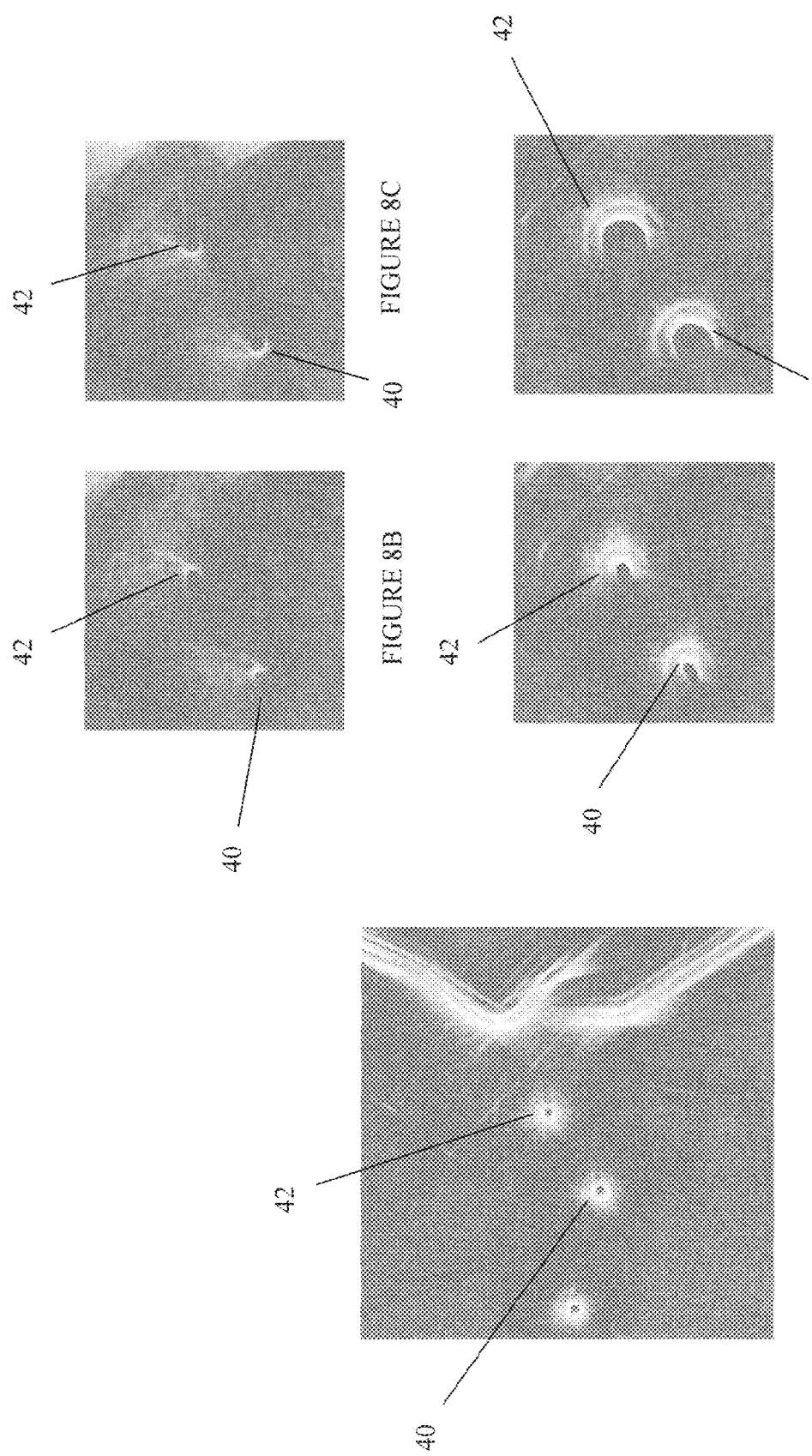

SYSTEM AND METHOD FOR IDENTIFICATION, GROUPING AND SIZING OF EMBEDDED FLAWS IN ROTOR COMPONENTS USING ULTRASONIC INSPECTION

CROSS REFERENCE TO RELATED APPLICATIONS

This application claims the benefit under 35 U.S.C. §119(e) of U.S. Provisional Application No. 61/753,620 entitled SYSTEM AND METHODS FOR IDENTIFICATION, GROUPING, AND SIZING OF EMBEDDED FLAWS IN ROTOR COMPONENTS USING ULTRASONIC INSPECTIONS filed on Jan. 17, 2013 which is incorporated herein by reference in its entirety and to which this application claims the benefit of priority.

FIELD OF THE INVENTION

This invention relates to nondestructive examination of rotors used in turbines and generators, and more particularly, to a method for ultrasonic inspection of a rotor which uses in-slice and inter-slice identification, grouping and sizing of any embedded flaws in the rotor.

BACKGROUND OF THE INVENTION

A rotor is a rotating component of a turbine or a generator. The reliability of a rotor is a major concern to turbine operators such as electric utilities. In order to promote operational safety and prevent potential failures, nondestructive examinations ("NDEs") are regularly performed to inspect the integrity of rotors and estimate the state of system integrity. A type of NDE includes the use of ultrasound techniques to detect flaws or defects in a rotor.

In an ultrasonic inspection, indications of any flaws or defects such as material discontinuities are detected through the use of ultrasound probes and are reported as digital information. The digital information is then evaluated to determine the size and shape of the flaws or defects. Performing the evaluation is not a trivial task and involves engineering know-how as well as experience. However, even with this know-how and experience, the evaluation is a time consuming process. In addition, many assumptions are made and safety factors are added to make a representative assessment of rotor integrity. As a result, many ultrasonic inspection systems are highly conservative with respect to data analysis in order to reduce risks. This results in inaccurate flaw size estimation and life prediction. In recent years, equipment life extension has become an important maintenance service aspect since a large number of rotors in electric utilities are close to reaching the limit of their original design life. Due to the substantial cost of replacing a rotor, it is desirable to extend the operating life of a rotor. In order to reliably predict a safe operating life of a rotor, the location and size of a flaw or defect needs to be estimated with high degree of accuracy. Accordingly, a more accurate and user friendly method for ultrasonic inspection of rotors is desirable.

SUMMARY OF THE INVENTION

Ultrasonic nondestructive examination (NDE) is regularly performed to inspect rotors used in turbines and generators for preventing catastrophic failures. A method and software system for flaw identification, grouping and sizing is developed for fatigue life assessment for rotors used in turbines and generators. The method includes providing ultrasonic data of a plurality of rotor slices and providing volume reconstruction of the ultrasonic data. The method also includes providing in-slice identification, grouping and sizing of flaw indications in the rotor based on the volume reconstruction. Further, the method includes providing inter-slice identification, grouping and sizing of the flaw indications based on the in-slice flaw indications and providing flaw location and size information. The method can be used in both phased-array and A-scan ultrasonic inspections.

BRIEF DESCRIPTION OF THE DRAWINGS

FIG. 4 depicts a scanning path of a phased array probe during a scanning operation for acquiring data.

FIG. 5 illustrates a side view of the phased array probe scanning a solid rotor having a solid rotor axis.

FIGS. 6A and 6B depict a test piece drawing and reconstruction result after all data has been fused.

FIGS. 7A-7F illustrate examples of unfused data.

FIGS. 8A-8E depict reconstruction results of first and second flat bottom drill holes each with a diameter of 2 mm.

DESCRIPTION OF THE INVENTION

Figure 1:
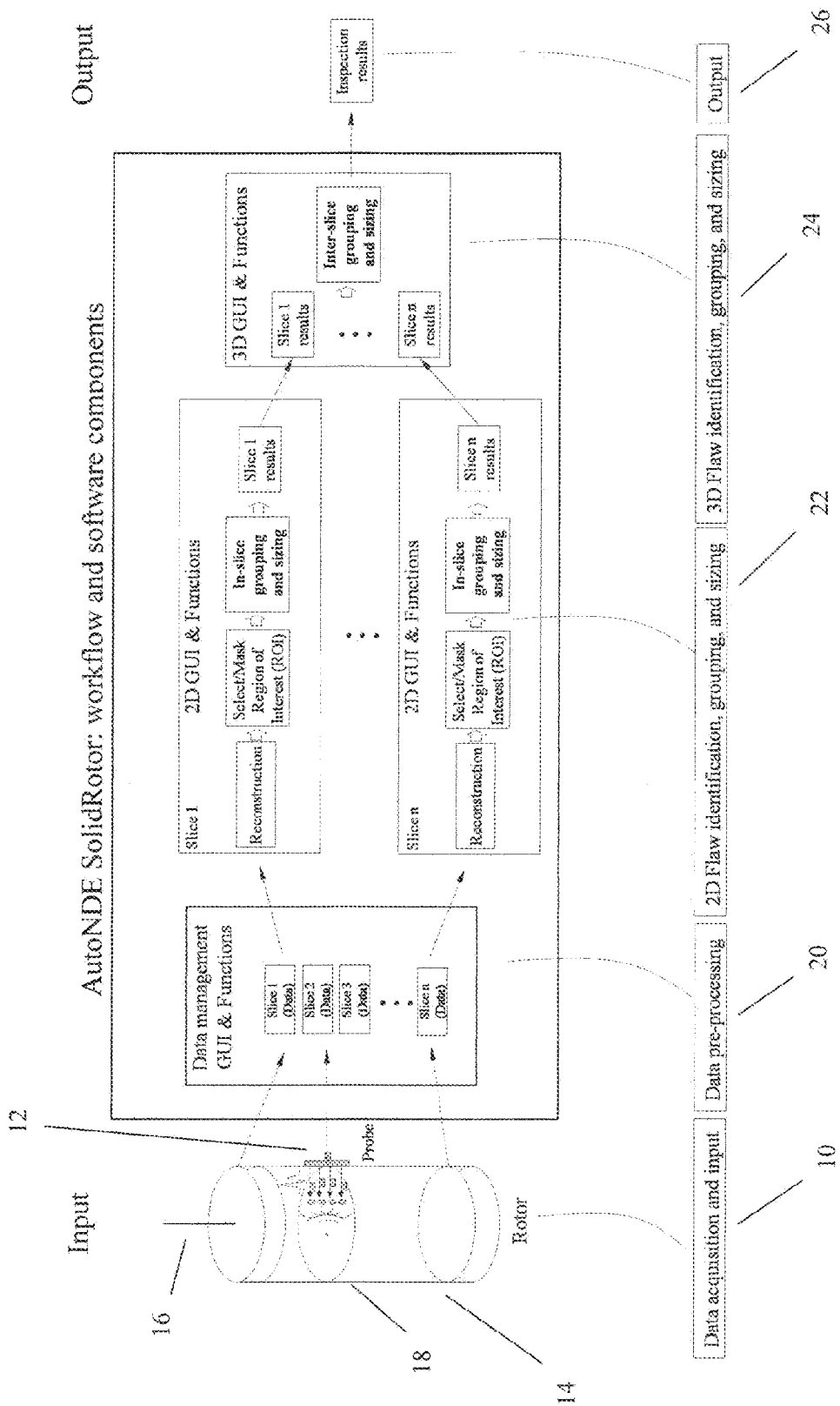
FIG. 1 depicts a method for reconstruction and flaw identification, grouping and sizing in accordance with the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. The terms "computer", "computer system", or "server" as used herein should be broadly construed to include any device capable of receiving, transmitting and/or using information including, without limitation, a processor, microprocessor or similar device, a personal computer, such as a laptop, palm PC, desktop, workstation, or word processor, a network server, a mainframe, an electronic wired or wireless device having memory and a storage device, such as for example, a telephone, an interactive television, such as for example, a television adapted to be connected the Internet or an electronic device adapted for use with a television, a cellular telephone, a personal digital assistant, an electronic pager, a digital watch and the like. Further, a computer, computer system, or system of this embodiment may operate in communication with other systems over a communication network, such as, for example, the Internet, an intranet, or an extranet, or may operate as a stand-alone system, virtual private network, and any other internetworked system. In the description below, like reference numerals and labels are used to describe the same, similar or corresponding parts in the several views of FIGS. 1-21.

INTRODUCTION

A rotor is the rotating part of a mechanical device. Rotors generally comprise a shaft with a plurality of blades extending radially from the shaft. Typically, a working fluid may move or be moved by the rotor blades. The shaft in these types of applications may be connected to an electricity producing device such as a generator.

The present invention relates to a visualization and analysis method and apparatus for automatic non-destructive examination of a rotor using ultrasound. A digital image is often composed of digital representations of one or more objects (or shapes). The digital representation of an object is often described herein in terms of identifying and manipulating objects. Such manipulations are virtual manipulations accomplished in the memory or other circuitry/hardware of a computer system. Accordingly, it is to be understood that embodiments of the present invention may be performed within a computer system using data stored within the computer system. In an ultrasonic rotor inspection, a large amount of data is captured. These data are manipulated to produce a three-dimensional representation in order to convey comprehensive 3D information enabling users to analyze the data efficiently and reliably. Embodiments of the present invention are described herein to provide an understanding of the visualization and analysis method and apparatus.

In an ultrasonic inspection performed as part on a non-destructive examination ("NDE"), indications of any flaws or defects such as material discontinuities are detected through the use of ultrasound probes and are reported as digital information. The digital information is then evaluated to determine the size and shape of the flaws or defects. Performing the evaluation is not a trivial task and involves engineering know-how as well as experience. However, even with this know-how and experience, the evaluation is a time consuming process. In addition, many assumptions are made and safety factors are added to make a representative assessment of rotor integrity. The difficulty of data analysis and evaluation lies in several aspects. These aspects include that the digital information is tremendously complex and intensive for manual interpretation. In addition, noise and irrelevant signals may introduce uncertainties. Further, spatial information is difficult to analyze.

Ultrasonic inspection data cannot easily encode geometry information of a target testing block that is being analyzed due to a large variety of possible shapes for the testing block. In particular, a user analyzing such data, such as an engineer, technician or other personnel, has to infer the location of a given indication by virtually mapping the data to the underlying geometry of the testing block. For objects with simple geometry configurations, virtual mapping may work well and provide relatively accurate results. However, virtual mapping could be difficult and inaccurate for complex geometries such as turbine blades. Improving flaw identification and sizing accuracy from ultrasonic inspection data is of great interest to the NDE industry. Reliable flaw identification and accurate flaw sizing is a key component for conditional-based maintenance and life-cycle cost reduction. The uncertainty in determining the size of a flaw may be handled through use a safety factor. However, use of a safety factor can sometimes be overly conservative thus increasing life-cycle cost. A technique for flaw identification, sizing, and shape estimation approaches is distance gain sizing ("DGS") and its variants. DGS is an echo amplitude based approach which uses the amplitude of ultrasonic signals for flaw estimation and is acceptable for flaws smaller than the transceivers beam size. Another approach is known as the Time-of-Flight diffraction ("TOFD") approach which is used to estimate the tip locations of a flaw. This information is then further explored to estimate the approximate shape of the flaw. TOFD can produce relatively accurate results for large flaws but shape information is very limited.

Ultrasonic inspections are conducted through the use of ultrasound transducers having mono- or dual-element crystals, which only have one fixed focal law and only capture data in a mode known as a 1D A-Scan. During an inspection, an ultrasound probe arrangement is used wherein a probe is moved manually or automatically by a scanner around areas of interest. However, a flaw under inspection is only hit by a relatively few A-Scan signals even when multiple probes are used. The information conveyed by A-Scans is relatively limited for characterizing the properties of a flaw.

A phased array ultrasound technique provides more information of a flaw by capturing reflection signal in a mode known as a 2D B-scan. In this technique, a phased array probe is used having a phased array ultrasound transducer arrangement that includes an array of crystal elements wherein each element is driven independently from other elements. By using a predetermined delay pattern while driving the array, different focal laws can be realized. A flaw is hit by substantially more ultrasound beams, and from different directions, when using a phased array probe than by using the probe arrangement used for an A-scan. This provides more information regarding a flaw, enabling a less conservative flaw analysis and more accurate flaw size estimation. A phased array probe has an advantage with respect to inspection of solid portions of a rotor. In a solid rotor inspection, some areas of interest are difficult to access due to attached turbine blades. Phased array probes can capture information in these areas flexibly by generating controllable focal laws for different depths and different incidence angles without substantially changing associated equipment such as a capturing device or wedge arrangement used in the ultrasound technique.

Analyzing data obtained from a phased array ultrasound technique is difficult. A difficulty is that in an inspection, a large amount of data is captured. The data is viewed image by image by a user to identify potential flaws, which is a tedious and time-consuming task. Another difficulty is that there are complicated spatial relations among captured images. In an inspection, an area is usually hit by multiple ultrasonic beams emitted from different positions. As a result, information regarding a flaw spreads in multiple B-mode images. Piecing together all information of the flaw hidden in these images can give accurate flaw size and shape estimation.

In the following description, a method for ultrasonic NDE is presented. Next, a 3D volume reconstruction method is described. Following that, flaw identification, grouping and flaw sizing methodology in accordance with the invention is described. After that, a software system implementing the introduced methods is described. In accordance with the current invention, the method may be used in both phased-array and A-scan ultrasonic inspections.

2. METHOD

Referring to FIG. 1, a method for reconstruction and flaw identification, grouping and sizing is shown. Step 10 of the method is directed to data acquisition and input. In this step, an ultrasound probe arrangement 12, such as a phased array probe, is used to collect data regarding a plurality of sections or slices of a rotor 14 each perpendicular to a rotor axis 16. For purposes of clarity, a single slice 18 is shown in FIG. 1. Each slice represents a circumferential ultrasonic scanning at a particular axial position. The captured data is then stored in a digital format in a computer.

Figure 2:
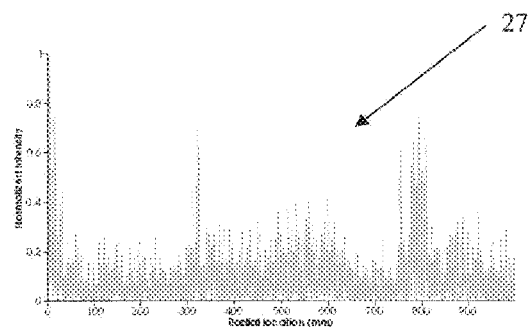
FIG. 2 depicts an exemplary A-Scan dataset that has been normalized.

At step 20, the data is then pre-processed. All data characterizing echo intensities of ultrasound are extracted from the data files and are normalized to the range between 0 and 1 (or more generally a range between $\alpha$ and $\beta$) according to the calibration setting of the ultrasound probe arrangement 12. For example, the recorded raw data may be in the range of [0, 65535] and one data point may have a value of 12035. The data point can then be normalized to 0.184 if the target range is [0, 1] or 46.8 if the target range is [0, 255]. Referring to FIG. 2, an exemplary A-Scan dataset 27 normalized to a range of [0, 1] is shown.

Figures 3A, 3B, 3C:
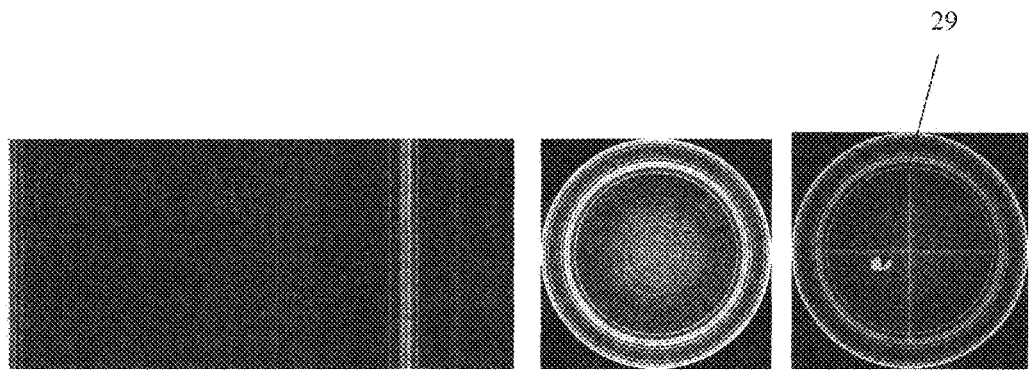
FIG. 3A depicts normalized data with a gray scale color map before reconstruction.
FIG. 3B depicts normalized data displayed with a gray scale color map after reconstruction.
FIG. 3C depicts selected regions of interest in FIG. 3B.

At step 22, 2D flaw identification, grouping, and sizing is performed. In particular, analysis is made in a 2D image plane for the data set associated with each of the slices. Each of the digitized data points in the data set is mapped to its physical position based on a calculation taking into consideration parameters of wave propagation speed, acquisition sampling frequency and an index of the data point. For example, given a discrete grid layout (e.g., an image with a dimension of M×N), the raw data will be mapped to elements of the grid. The resulting output from the geometric mapping module is, for example, an image of size M×N. Further, each element (pixel) of the grid (image) has an intensity value which can be color coded using a color map. This enables visualization of data in a correct geometry setting since without this mapping the physical position of a data point is not quantified. The effect of mapping is shown in FIGS. 3A-3C. In particular, FIG. 3A depicts normalized data with a gray scale color map before reconstruction. FIG. 3B depicts normalized data displayed with a gray scale color map after reconstruction. FIG. 3C depicts selected regions of interest 29 in FIG. 3B. The reconstruction consists of mapping, and other operations such as smoothing and other image processing techniques as will be described in Section 3 of the current patent application.

After 2D reconstruction, regions of interest ("ROI") can be specified to focus analysis to small regions instead of the entire image. It is also possible that the entire image is treated as one region of interest thus performing the following analysis using the entire image. After the region of interest selection process, in-slice flaw identification, grouping, and sizing are performed as will be described in Section 4.2 to identify a flaw and estimate flaw size. The results of this step are saved.

At step 24, 3D flaw identification, grouping, and sizing is performed. After all participating 2D slices are analyzed, a 3D (spatial) analysis may be performed. 3D analysis is not mandatory and is based on actual requirements and applications. If two slices are separated by a large distance, or there is only one slice is available, 3D analysis will not provide additional information. Aspects of the 3D analysis such as inter-slice grouping and sizing will be described in Section 4.3.

At step 26, final results of the entire analysis cycle are output. The output provides information about flaws such as their location and size for further fatigue life assessment and structural reliability estimation.

3. 2D/3D VOLUME RECONSTRUCTION AND VISUALIZATION

With respect to 2D/3D volume reconstruction and visualization, the disclosure of U.S. application Ser. No. 12/903,501 (U.S. Patent Application Publication No. 2011/0087443 A1) filed on Oct. 13, 2010 entitled THREE-DIMENSIONAL VISUALIZATION AND ANALYSIS METHOD AND SYSTEM FOR NON-DESTRUCTIVE EXAMINATION OF A ROTOR BORE USING ULTRASOUND is incorporated herein by reference in its entirety. 2D volume reconstruction involves a process of reading raw NDE data resulting from scanning at one axial position, mapping dimensionless data points to their correct geometric positions, formulating an image and storing the image data. 3D volume reconstruction is similar to the 2D volume reconstruction with an additional aspect in that the 3D volume reconstruction process maps raw data points to a spatial position.

With respect to data acquisition, the number of possible locations for an ultrasonic transducer is limited due to the existence of the turbine blades. However, a phased array probe provides the capability to send out and receive sound waves from a plurality of angles thus allowing the capture of data beneath the turbine blades. Referring to FIG. 4, a scanning path 30 of a phased array probe 28 during a scanning operation for acquiring data is shown. In one embodiment, the scanning path 30 is circular. In FIG. 4, an end view of a solid rotor 32 is shown and the scanning path 30 may correspond to an outside diameter surface 34 of the solid rotor 32. Further, more than one phased array probe may be used. Referring to FIG. 5, a side view of the solid rotor 32 having a solid rotor axis 36 is shown. The solid rotor 32 may have different sized sections. The phased array probe 28 performs 2D B-scans 38 at different angles of incidence while rotating around the solid rotor axis 36 at different capture positions as depicted in FIGS. 4 and 5. The number of capture positions and/or ultrasound probes around the solid rotor axis 36 and the number of B-scans at different angles of incidence may vary. Furthermore, different ultrasound probes or wedges might be used at different axial positions. Acquisition set-up data and the captured data of each axial position is stored in an individual raw data file. Each 2D B-scan at each angle of incidence may be considered as a composition of individual 1D A-scans. As a consequence, a sampling grid is highly irregular which makes high demands on a reconstruction algorithm. A reconstruction algorithm may be used that can make use of several sampling methods for mapping. The data acquired by the phased array probe 28 can be highly dense depending on the sampling frequency. The resulting image quality depends on the data acquired by the phased array probe, the actual dimensions of the target being tested and the dimensions of the image. If the image dimension is very large, the elements (pixels) of the grid (image) may not be filled with any raw data points. If the image dimension is too small, the resolution of image will be small and the sizing of a suspicious flaw area may be inaccurate resulting in possible loss of the detail of the flaw area. An appropriate determination of the resulting image dimension may be based on a criterion that each of the elements in the grid being filled by at least one data point. In general, two fundamental principles may be used for mapping such as, for example, those described by Westover, L. in "Footprint Evaluation for Volume Rendering", ACM SIGGRAPH Computer Graphics, Volume 24 Issue 4, August 1990, pgs. 367-376, ("Westover"), the contents of which are incorporated herein by reference in their entirety. One approach is a backward mapping algorithm which maps the image into a data space by searching the nearest sample position in the data space. Another approach is a forward mapping algorithm which maps the data to an image space by identifying the image space sample positions that are affected by a data space sampling position. As the phased array probe acquired data is highly irregular in terms of the sampling position, the backward algorithm is very time consuming and the forward algorithm is usually adopted. In particular, the forward algorithm has smaller computational demands.

3.1 Volume Splatting-Based Reconstruction

The reconstruction algorithm is based on the assumption that every sample point in the data space represents the signal of a certain spatial region. When mapped to the image space, it can affect multiple image space sampling points but its influence decreases over distance. Each sampling point has a certain footprint in form of a 3D volume known as a kernel. Depending on the sampling rate in different dimensions the kernel can be formed either isotropic or elliptical. In the following, the kernel is weighted with the value of a current sample point. The contributions of all footprints on the regular grid are then averaged. This approach is known as elliptical weighted average volume splatting ("EWA volume splatting"). For example, see previously referenced Westover and Greene, N., Heckbert, P., "Creating Raster Omnimax Images from Multiple Perspective Views Using the Elliptical Weighted Average Filter", Computer Graphics and Applications, IEEE, Volume 6, Issue 6, 1986, pgs. 21-27 and Zwicker, M., Pfister, H., Van Baar, J., Gross, M., EWA Splatting, Visualization and Computer Graphics, IEEE Transactions on Volume 8, Issue 3, 2002, pgs. 223-238, the contents of which are incorporated herein by reference in their entirety. Due to speed optimization a triangle kernel function is used instead of the Gaussian function which is used in the original approach. Averaging may be misleading in the case of single signal peaks, e.g. cracks which can only be seen from one angle, because the peaks can be eroded which can lead to a vanished flaw. For this reason a more conservative maximum approach is implemented. This is used to ensure that single signal peaks appear in the result regardless of the surrounding data. A disadvantage of this approach is high noise sensitivity. Referring to FIGS. 6A and 6B, a testpiece drawing and reconstruction result after adjustments, respectively, are shown.

As mentioned above, the data structure is very complex. FIGS. 7A-7F illustrate examples of unfused data. FIGS. 7A-7C depict so called fans (i.e. polar B-scans taken at one capture position). FIGS. 7A-7C depict the same volume from different angles. In particular, it has been that it is difficult to find corresponding points or portions among the figures. FIGS. 7D-7F illustrate a reconstruction result when using only one focal law (angle of incidence) when rotating around an axis. FIG. 6B shows the corresponding reconstruction result after all data has been fused. It has been found that it is difficult to determine flaw sizes and positions using unfused data. Therefore, it is important to capture data from different orientations as enabled by a phase array probe and to then fuse the data.

Flaw size, shape and orientation estimation requires a high degree of accuracy in the determination of data acquisition settings. FIGS. 8A-8E depict reconstruction results of first 40 and second 42 flat bottom drill holes each with a diameter of 2 mm. It is noted that FIGS. 8B-8E illustrate a partial region of FIG. 8A including the holes 40, 42. For the reconstruction, an EWA volume splatting algorithm was used. FIG. 8A shows the reconstruction result with adjusted angle and speed of sound values (−2.25%). FIG. 8B shows an initial reconstruction result. FIG. 8C shows the result after speed of sound adjustment. FIGS. 8D and 8E are both angular adjusted. The speed of sound value in FIG. 8E is adjusted to +2.25%.

FIG. 8B shows the result adjusted for speed of sound parameter but without wedge angle correction. In particular, the speed of sound in the metal is not accurate and a wedge angle were not set correctly. The holes 40, 42 are open and the signal spreads widely. The wedge offset is −4.0 degrees. The result due to wedge offset adjustment can be seen in FIG. 8D. The holes 40,42 are still open, but the signal is more concentrated around each hole 40,42. Adjustment of the speed of sound is important. As the holes 40,42 themselves are relatively small, relatively minor changes in the speed of sound value could cause variances in size estimation which are larger than the flaw size. FIG. 8A shows the result with adjusted parameters. The offset is −2.25%. Changing the offset to +2.25% will lead to a substantially different diameter estimation (FIG. 8E).

As these results show, parameter adjustment is an important factor for size estimation of small flaws. Although flaw position varies too, it is, because of the high number of measurements, easier to determine. For this reason DGS and other amplitude based methods are typically used for small flaws. For larger flaws, echo dynamic pattern or time-of-flight flaw sizing methods may be used. See Song, S., Schmerr, L., "An Ultrasonic Time-of-Flight Equivalent Flaw Sizing Method", Journal of Research in Nondestructive Evaluation, Volume 4, Issue 1, 1992, pgs. 1-18. Due to the large number of RDTiff files involved in one project, the file size of each RDTiff is very important. The size is basically determined by the sampling rate. FIGS. 7A-7F show examples of sample rate reduction. The data can be scaled through the number of sampling points on each A-scan, the number of capture positions around the rotor and/or through the number of angles of incidence at each capture position.

3.2 Direct Maximum Intensity-Based Reconstruction

Alternatively, direct maximum intensity-based reconstruction may be used wherein each of the sampled points is assigned to its corresponding pixels in the image. The location of the pixel for a given sampled point is computed using the scan surface geometry, sound speed, sampling frequency and offsets of an exit index from the probe. No post-processing filters such as splatting or averaging is applied. If multiple sample points hit an identical pixel of the image, only the maximum amplitude of these points is used for the pixel. Therefore, the maximum intensity is retained for each of the pixels in the image. This technique is straightforward and relatively simple to implement and as such it is fast and can be processed in parallel.

The direct maximum intensity-based reconstruction is more sensitive to noise components in the recorded data and parameters related to probe position and offset. A slight difference between the actual probe position (and exit index) and the setting values for position (and exit index) can propagate to a larger difference in the image due to the high speed of sound path. Therefore, this method usually does not estimate the flaw size and shape from the volumetric flaw region but uses only the maximum intensity the volumetric flaw region to evaluate the equivalent reflector size.

4. FLAW IDENTIFICATION 4.1 Flaw Identification

Figure 9:
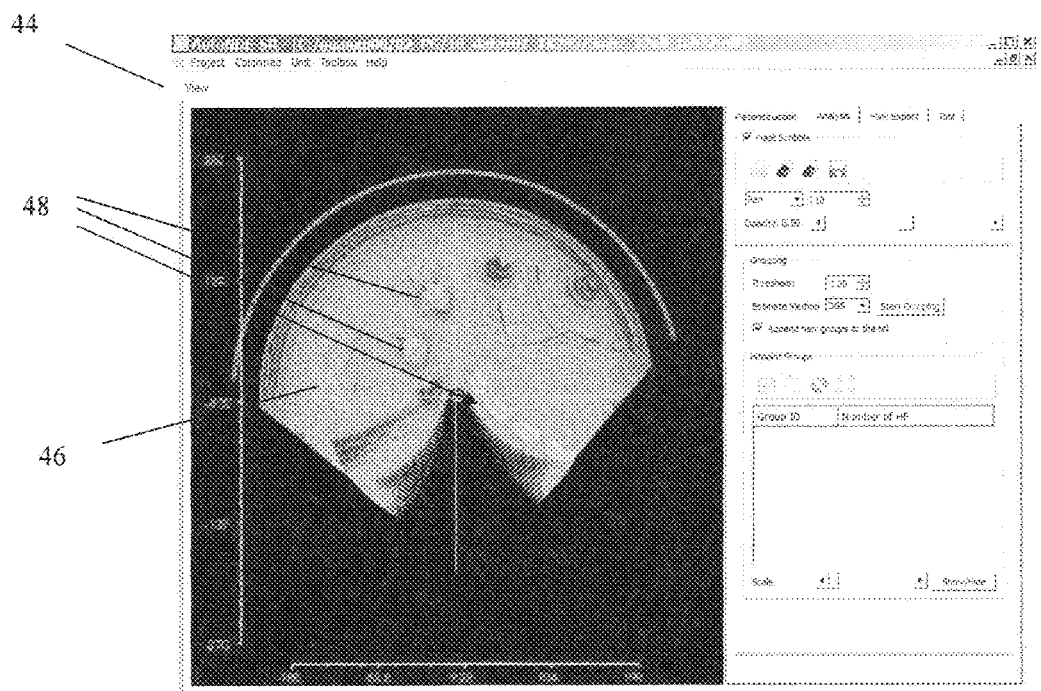
FIG. 9 depicts an exemplary volumetric image with annotated regions of interest.

Flaw identification refers to a process of extracting information about the existence, location, characteristics of flaws in a testing piece. Flaw identification may use both the raw dataset and the reconstructed dataset, i.e., volumetric image previously described in section 3. If the volumetric image is reconstructed with very high resolution parameters, using reconstructed volumetric image can be equivalent to using the raw dataset. The method of flaw identification is based on ultrasonic data features such as an amplitude of the echo intensity. A predefined threshold, for example, α=40%, is used to locate all data points in the raw dataset or reconstructed volumetric image. Given the range of the echo intensity [a b], the data are normalized to the range of [0 1]. Using the reconstructed volumetric image as an example, each voxel having an intensity larger than a will be identified as a hit point ("HP"). A global or local searching is performed to find all HPs in the volumetric image. For each HP, information about the physical location of the voxel, the indexes of the voxel in the image and the normalized intensity is stored. Alternatively, only ROI are searched instead of the entire volumetric image. Using ROI allows for efficient flaw identification when the entire volumetric image is very large. Referring to FIG. 9, a computer display 44 of an exemplary volumetric image 46 is shown. In FIG. 9, exemplary ROI are shown annotated in the image. Determination of the ROI is based on the judgment of a user by visualizing the reconstructed images.

4.2 In-Slice Grouping and Sizing

Figure 10:
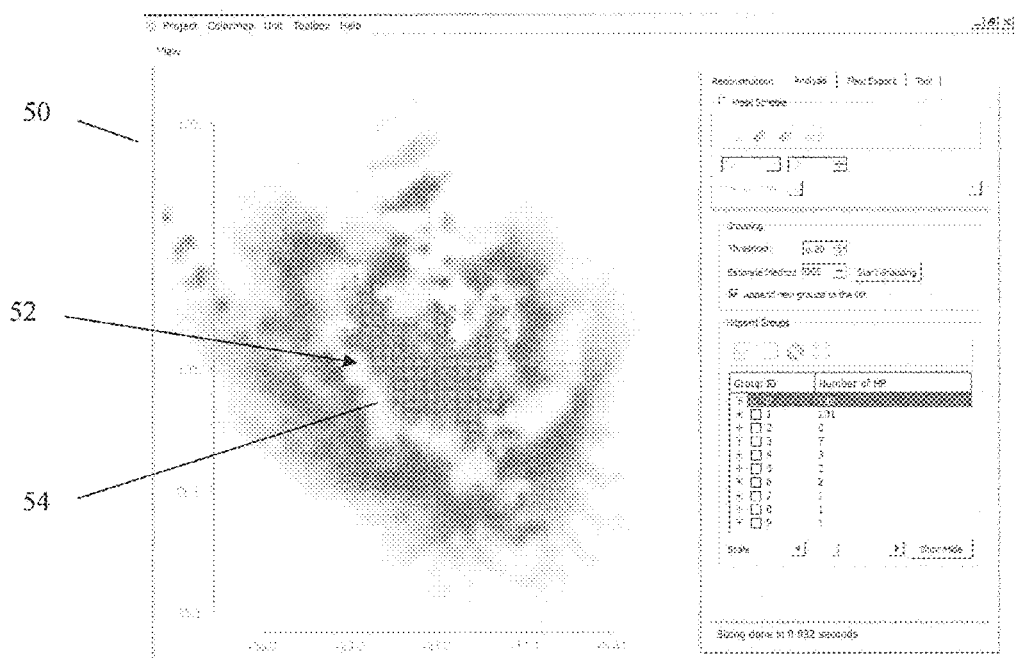
FIG. 10 depicts a plurality of hit points forming a hit point cluster after in-slice grouping is performed.

Since multiple HPs may be connected (in terms of adjacent voxels) due to the shape and extent of a flaw and the scattering nature of ultrasonic waves, connected HPs should be clustered together due to a large probability that those HPs are generated from one individual flaw. This clustering process refers to the in-slice grouping shown in FIG. 1. In-slice grouping is based on the voxel/pixel connectivity of each of the HPs. Known region-growing methods or similar algorithms can be used to find all in-slice groups. For example, see Adams, R., Bischof, L., "Seeded Region Growing", Pattern Analysis and Machine Intelligence, IEEE Transactions on Volume 16, Issue 6, 1994, pgs. 641-647, the contents of which are incorporated herein by reference in their entirety. Referring to FIG. 10, a computer display 50 is shown which depicts a plurality of HPs 52 to form an HP cluster 54 after in-slice grouping is performed.

Flaw sizing for each of the HP groups is based on using the HP with maximum intensity and a known distance-gain-size (DGS) method. For example, see Krautkrämer, J., "Determination of the Size of Defects by the Ultrasonic Impulse Echo Method", British Journal of Applied Physics Volume 10, Issue 6, 2002, pgs. 240-245, the contents of which are incorporated herein by reference in their entirety. After sizing, each of the HP groups has an equivalent reflector size ("ERS"). The DGS method involves using a calibration hole with a known size (diameter) and calibration testing. In the calibration process, the echo intensity from a calibration hole with a known size, e.g., a diameter of $d_0$, is calibrated to produce an echo amplitude of $h_0$ with a calibration signal intensity $I_0$. Given a base signal intensity I, the calibration gain is:

$$g_0 = 20\log\left(\frac{I_0}{I}\right), \tag{1}$$

which leads to:

$$I_0 = I 10^{\frac{g_0}{20}}. \tag{2}$$

Assuming the ultrasound inspection of an actual flaw size gives an echo amplitude of $h_1$, the inspection gain is:

$$g_1 = 20\log\left(\frac{I_1}{I}\right), \tag{3}$$

leading to:

$$I_1 = I 10^{\frac{g_1}{20}}. \tag{4}$$

The reflector area for the calibration hole is denoted as $S_0$ and the equivalent reflector area for the actual flaw as $S_1$. It is known that $S_0 I_0 \propto h_0$ and $S_1 I_1 \propto h_1$ and the following equations can be established:

$$\frac{S_1 I_1}{S_0 I_0} = \frac{h_1}{h_0} \tag{5}$$

and $$\frac{\frac{1}{4}\pi d_1^2 I 10^{\frac{g_1}{20}}}{\frac{1}{4}\pi d_0^2 I 10^{\frac{g_0}{20}}} = \frac{h_1}{h_0}, \tag{6}$$

where $d_1$ is the equivalent reflector size of the actual flaw. As a result, $$d_1 = d_0 \sqrt{\frac{h_1}{h_0}} 10^{\frac{g_0 - g_1}{40}}. \tag{7}$$

The flaw area is computed as:

$$S_f = \tfrac{1}{4}\pi d_1^2. \tag{8}$$

For example, given the calibration hole size $d_0$=2 mm, the calibration gain $g_0$=15 dB and the calibration echo amplitude $h_0$=80%, testing is performed and the inspection gain is $g_1$=10 dB and the echo amplitude of an indication is $h_1$=100%. Using Eq. (7), the ERS of the indication is calculated as $d_1$=2.98 mm. The reflector area is treated as the flaw area and is quantified as $\frac{1}{4}\pi d_1^2$=6.98 mm$^2$.

4.3 Inter-Slice Grouping and Sizing

NDE scan follows a physical pattern or path on the testing block. In typical scan geometry settings for rotor components, the scan path cannot always cover the entire testing object and the reconstructed image can also be discrete. One typical example is described as follows. The automatic scan of a rotor (cylinder) starts from an axial position (e.g., 10 mm from an end of the rotor). An ultrasound probe is moved precisely around a circular path and the plane of the circular path is perpendicular to the center axis of the rotor. After the probe returns to its initial position, the data sampled covers the entire plane and the data can be considered as one slice. The probe moves to the next axial position (e.g., 15 mm from the end of the rotor) and repeats the circular movement to obtain another slice. This process continues until the axial range of query is fully covered. In this example, the incremental step along the axial direction is 5 mm, but can be set to a larger step size or a smaller step size. However, a smaller step size results in a larger data file and longer testing time. A larger step size results in a low resolution in axial direction. Selection of a suitable step size may be based on a user's experience and judgment. But, regardless of the step size chosen, the axial slices are discrete both physically or in a volumetric image. A long flaw extending in axial direction can become segmented in the resulting reconstructed slice images due to the discretization in axial movement of the probe. Therefore, a grouping method is considered to assemble segmented flaw indications into one large flaw.

Figure 11:
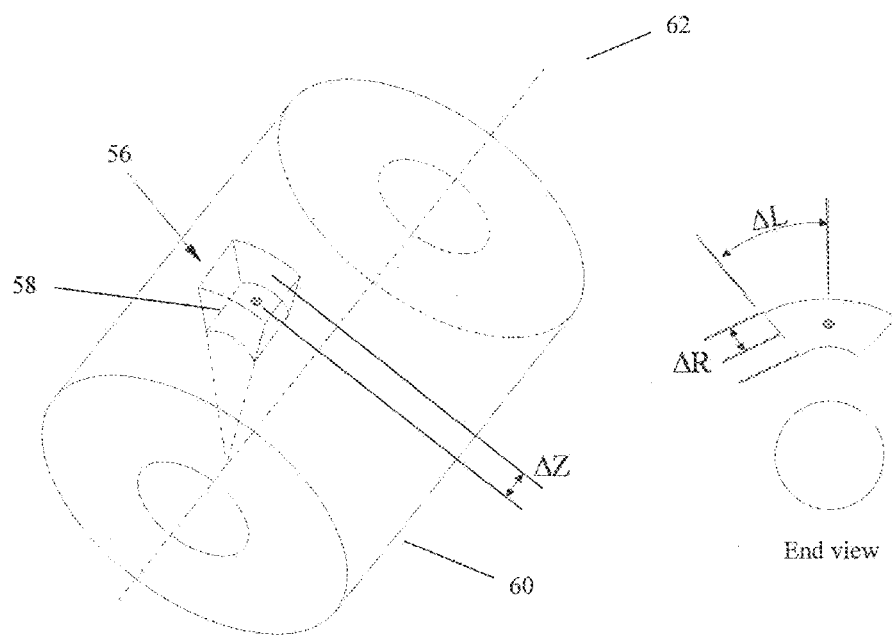
FIG. 11 shows a rectilinear grouping envelope in accordance with the invention.

In inter-slice grouping, discrete flaw clusters (i.e., in-slice indications) are grouped according to a predefined shape and form a new flaw group. The predefined shape is devised based on probe location, wave scatter property, as well as expert and historical experience. Referring to FIG. 11, a rotor 60 having a center axis 62 is shown. The predefined shape may be a rectilinear grouping envelope 56 which includes a hit point or flaw indication 58. The rectilinear envelope 56 is defined by three parameters, $\Delta Z$, $\Delta R$, and $\Delta L$, as shown in FIG. 11. $\Delta Z$ and $\Delta R$ refer to a distance along axial and radial directions, respectively, between an edge of the rectilinear envelope 56 and the flaw indication 58. $\Delta L$ is half of the arc length of the outside edge of the rectilinear envelope 56 which is centered on flaw indication 58. A grouping algorithm is then utilized as set forth in the following description. In the following steps, an interaction refers to when two flaw indications fall in to the same rectilinear envelope 56. At first, all in-slice indications are loaded into memory. Next, a first indication is checked against each successive indication for interaction. The indications that interact with the first indication are assigned the same group number as the first indication. This process is then repeated for a second indication, a third indication, etc. until all the indications have been checked. The indications that do not interact are assigned a separate group number. In this manner, each indication is checked against every other indication for interaction. This enables a determination as to whether a flaw from one slice extends to a successive slice. When the process is complete, the data in memory will be in group order, ready to be written to an output file or used for further processing. In one embodiment, a hit point is considered a flaw indication if there is only one hit point in a group. If there are multiple hit points in a group, the entire group is considered a flaw indication.

Figure 12:
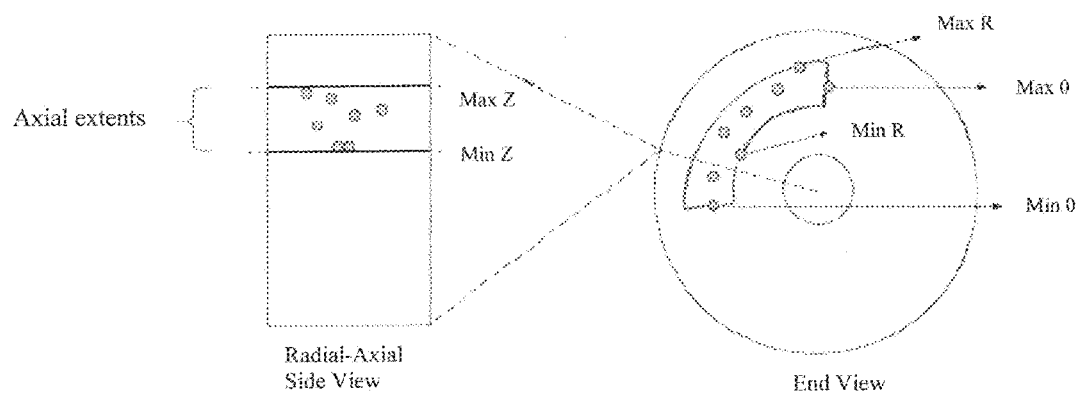
FIG. 12 shows a radial and axial extent from the rectilinear grouping envelope.

After inter-slice grouping, flaw groups will be reported and the information will be used for flaw sizing. The sizing for inter-slice flaw groups is different than that of the in-slice flaw groups. Recall the sizing for in-slice groups is based on the DGS method and the HPs with maximum intensity within an in-slice flaw group are used. For inter-slice grouping, the physical extents of an inter-slice group is used. Referring to FIG. 12, for each of the inter-slice group, the radial extent is obtained as (Max R–Min R), and the axial extent is obtained as (Max Z–Min Z). The maximum elliptical area enclosed by the rectangular can be calculated as:

$$S_f = (\text{Max } R - \text{Min } R)(\text{Max } Z - \text{Min } Z). \quad (9)$$

For example, given an inter-slice group with extents of Max R=303 mm, Min R=301.5 mm, Max Z=1117 mm, and Min Z=1102 mm, the flaw area is $S_f$=22.5 mm$^2$.

The flaw area $S_f$ is then treated as an embedded elliptical crack area for further fracture mechanics analysis. It is also possible that no inter-slice group is found by the inter-slice grouping process. In such a case, the in-slice sizing result is directly used as an embedded elliptical crack area for further fracture mechanics analysis. In an embodiment, Eq. (9) is used to obtain $S_f$. $S_f$ can then be substituted in Eq. (8) to calculate $d_1$.

5. AUTONDE-SOLIDROTOR COMPUTER SOFTWARE

Figures 13, 14:
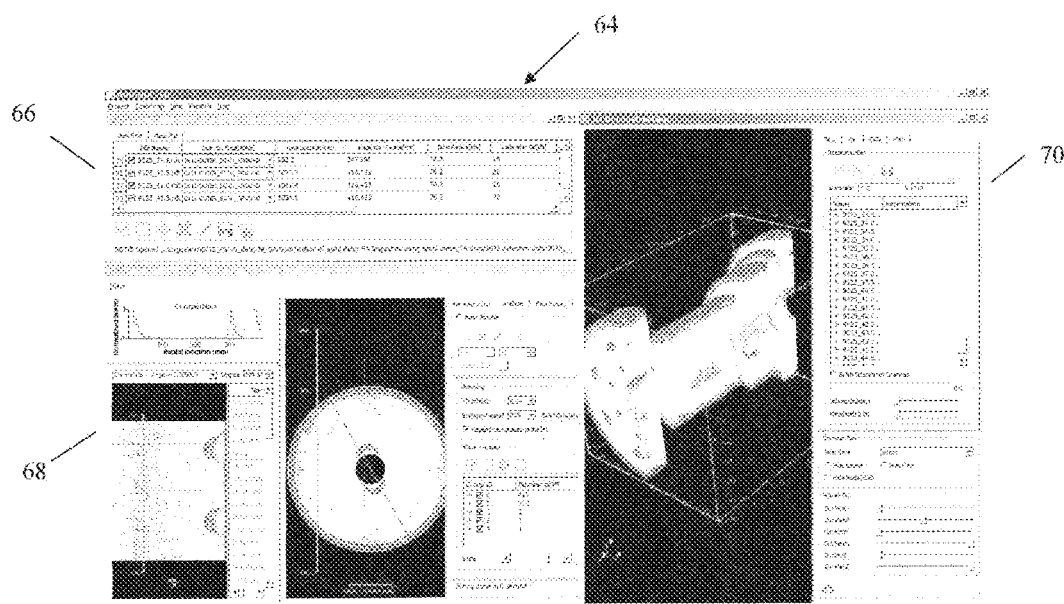
FIG. 13 is an overview of a graphical user interface ("GUI") which depicts a data management interface, 2D reconstruction and visualization interface and 3D reconstruction and visualization interface.
FIG. 14 depicts a GUI interface for data management.

Software, known as AutoNDE-SolidRotor, was developed to implement the described data reconstruction, and flaw identification, grouping and sizing methods. Referring to FIG. 13, an overview of a graphical user interface (GUI) 64 for the software is shown. In FIG. 13, a data management interface 66, 2D reconstruction and visualization interface 68 and 3D reconstruction and visualization interface 70 are shown.

Figure 15:
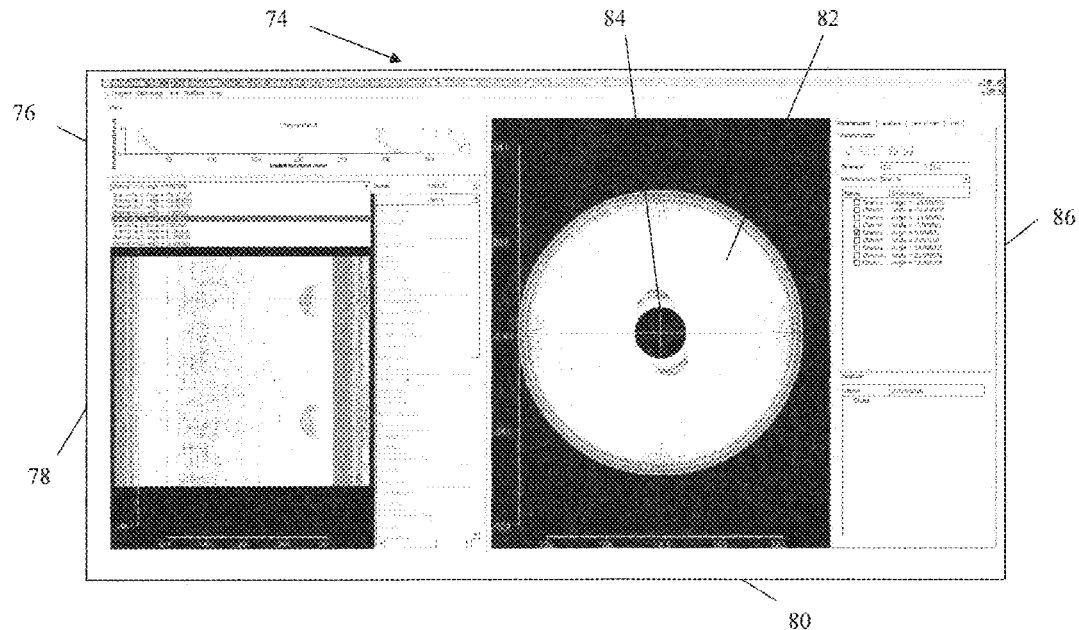
FIG. 15 shows a 2D configuration and reconstruction panel.
Figure 16:
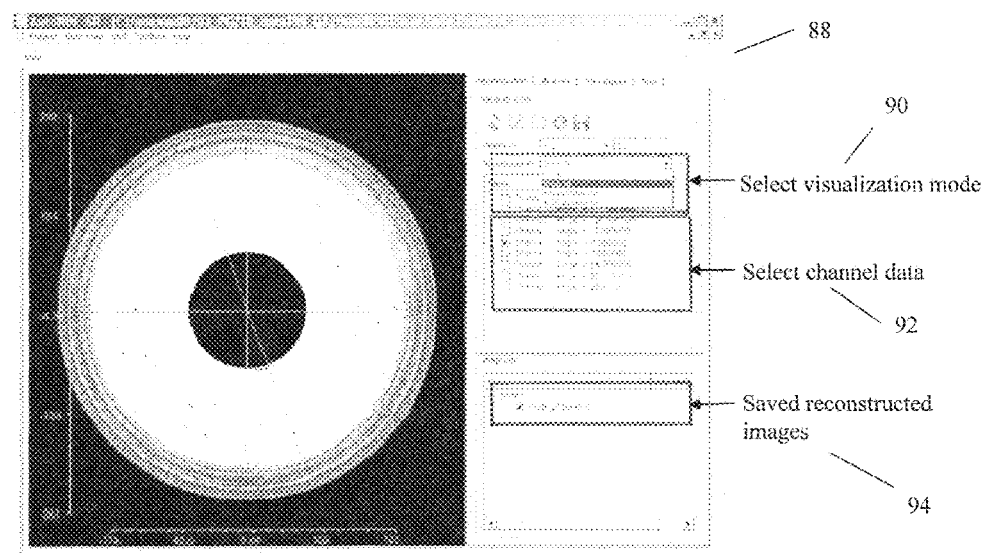
FIG. 16 shows a 2D reconstruction interface that allows for selection of channels and visualization modes.
Figure 17:
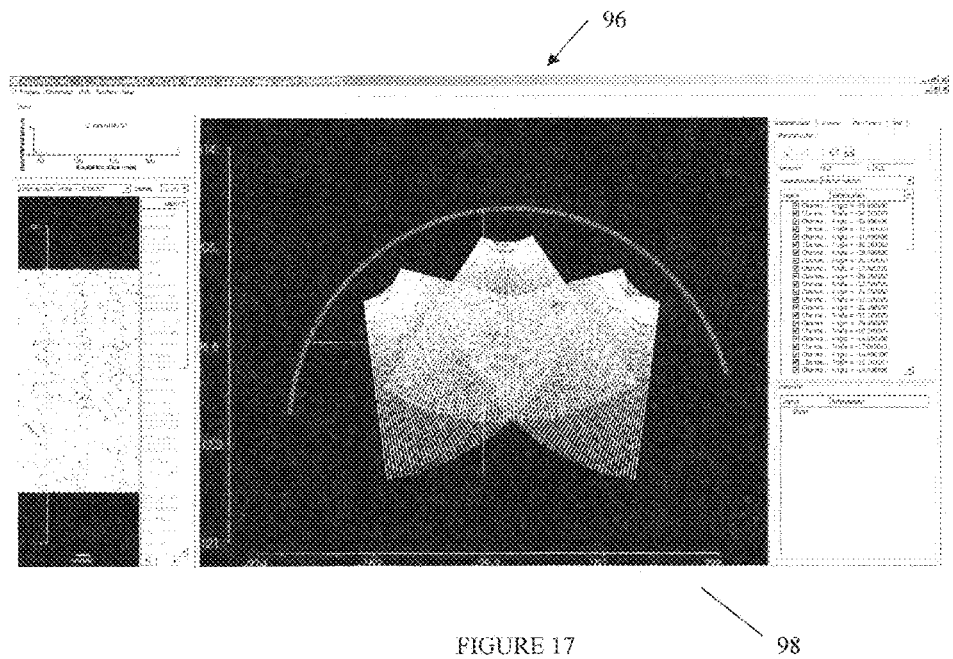
FIG. 17 depicts a 2D reconstruction interface in a scan position selection mode.

FIG. 14 presents a GUI interface for data management 72. The interface 72 allows for import of raw inspection data and configuration of parameters for each of the raw data. The parameters may include the type of scan movement, axial position of the scan, inspection radius of the scan, bore radius of the rotor and calibration information. Using the interface 72, a user can easily launch a 2D GUI interface and a 3D GUI interface. FIG. 15 shows a 2D configuration and reconstruction panel 74. The 2D interface is used to create a slice image based on the data captured at one axial location of the rotor component. Data points in the raw data are mapped to the correct geometry locations using the information regarding sound speed, sampling frequency, inspection radius, and the basic geometry of the inspected rotor such as outside diameter and bore diameter (if the rotor has a bore). Raw A-scan data 76 are shown in the left top region of the panel 74 and aw B-scan data 78 are shown in the left bottom region of the panel 74 in a 2D rectangle. A reconstructed 2D image 80 is shown in the right side of the panel 74, showing a rotor 82 with a bore 84. The very right of the panel 74 presents a current configuration of the reconstruction 86. The configuration can be used to select data from different channels of the phased-array data file. Some advanced features are also implemented to help users inspect the data in different modes. A 2D reconstruction interface 88 that allows for selection of channels and visualization modes is shown in FIG. 16. In particular, a user is able to select a visualization mode 90, channel data 92 and view saved reconstructed images 94. FIG. 17 depicts a 2D reconstruction interface 96 in a scan position selection mode 98. In this mode 98, inspection data of all channels or selected channels is displayed.

Figure 18:
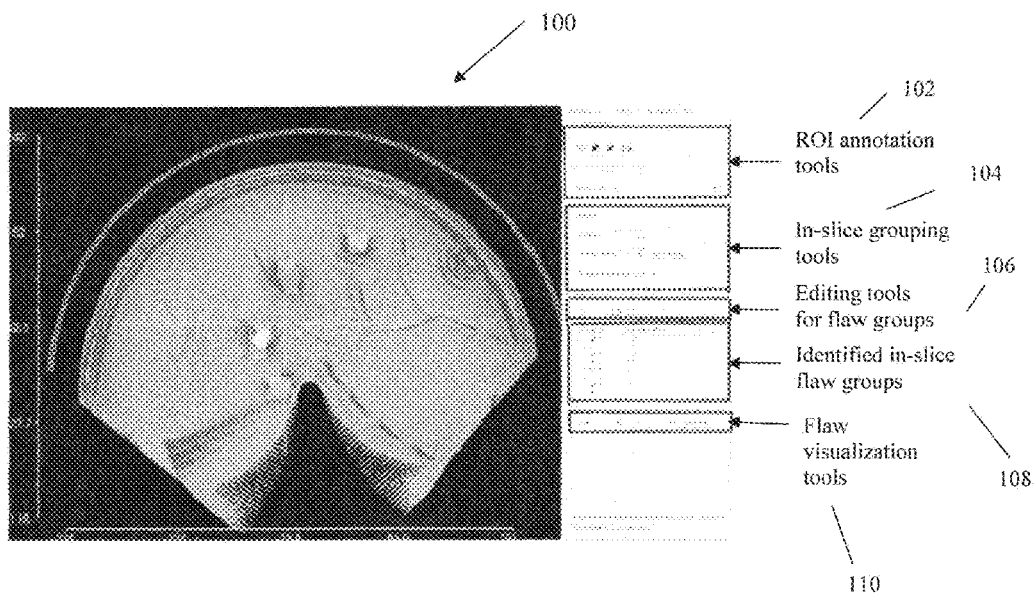
FIG. 18 illustrates a 2D reconstruction interface for flaw identification and in-slice grouping.
Figure 19:
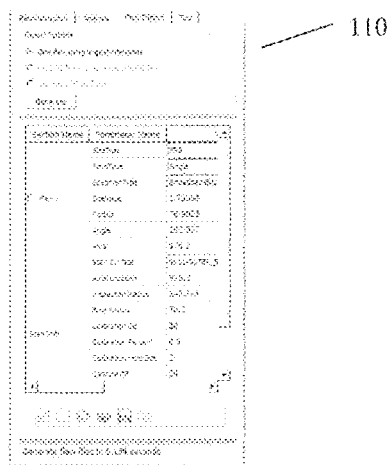
FIG. 19 illustrates an export interface.

FIG. 18 illustrates a 2D reconstruction interface 100 for flaw identification and in-slice grouping. The interface 100 includes ROI annotation tools 102, in-slice grouping tools 104, editing tools for flaw groups 106, a display of identified in-slice flaw groups 108 and flaw visualization tools 110. The interface 100 allows annotation of ROI such as by masking a region interactively and erasing a masked region interactively. The interface 100 also allows for saving annotation results for later use. In the in-slice grouping tools 104, a threshold can be setup for intensity. In-slice grouping results are displayed in a tree structure and the results may be edited by users. For example, if two groups are very close, a user can merge the two groups (or several groups) into one based on experience and know-how. A group can also be deleted if it is irrelevant. After one working slice is finished for analysis, the results can be exported to a text format for information storage or further inter-slice grouping. An export interface 110 is shown in FIG. 19.

Figure 20:
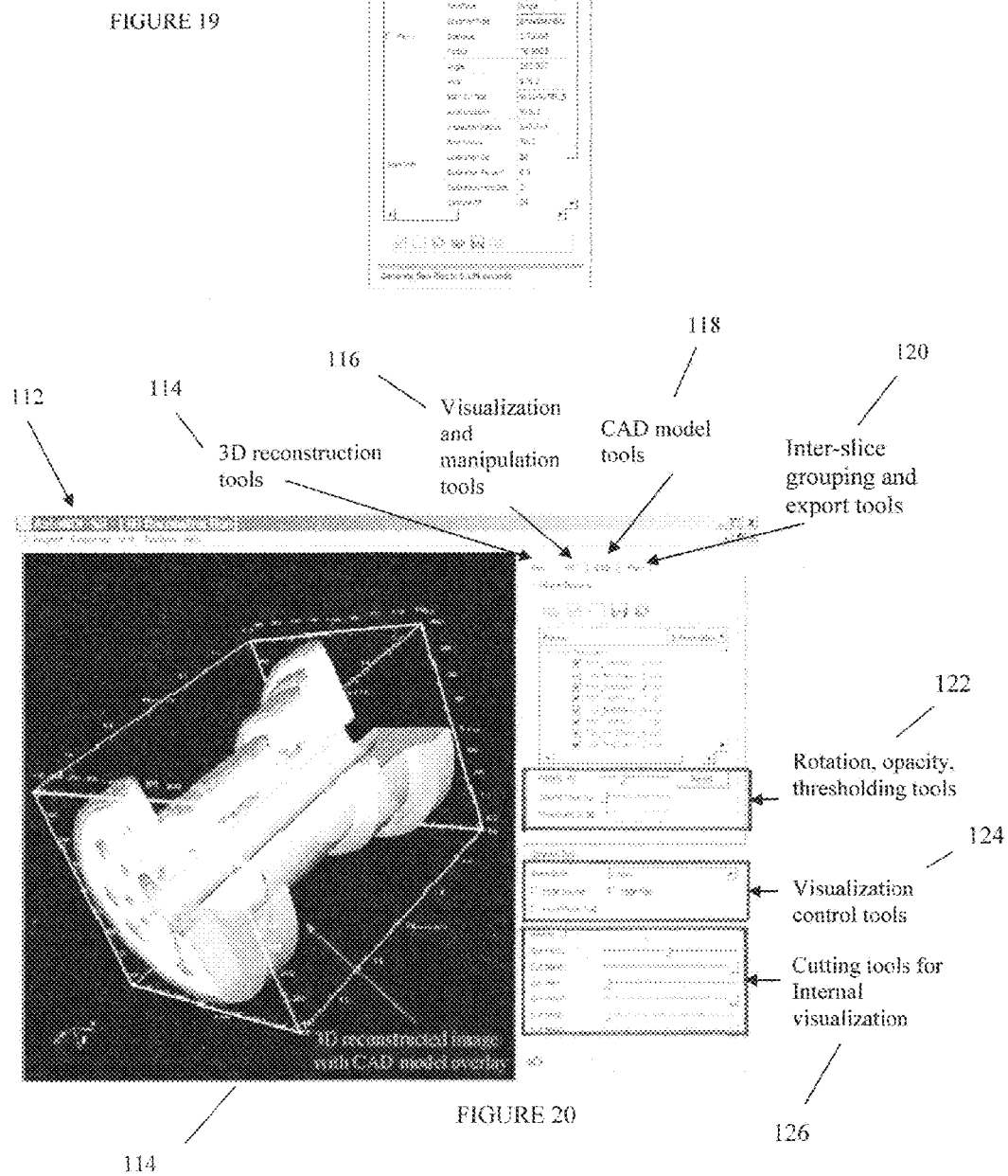
FIG. 20 depicts an overall 3D GUI interface which includes 3D reconstruction tools, visualization and manipulation tools, CAD model tools, inter-slice grouping and export tools, rotation, opacity and thresholding tools, visualization control tools and cutting tools for internal visualization.

FIG. 20 depicts an overall 3D GUI interface 112. In FIG. 20, a 3D reconstructed image with CAD model overlay 114 is shown as an example. The 3D interface 112 includes 3D reconstruction tools 114, visualization and manipulation tools 116, CAD model tools 118, inter-slice grouping and export tools 120, rotation, opacity and thresholding tools 122, visualization control tools 124 and cutting tools for internal visualization 126. In particular, the 3D interface enables 3D visualization, navigation, volumetric cutting, rotation, CAD model overlay, inter-slice grouping, result exporting and other functions.

Figure 21:
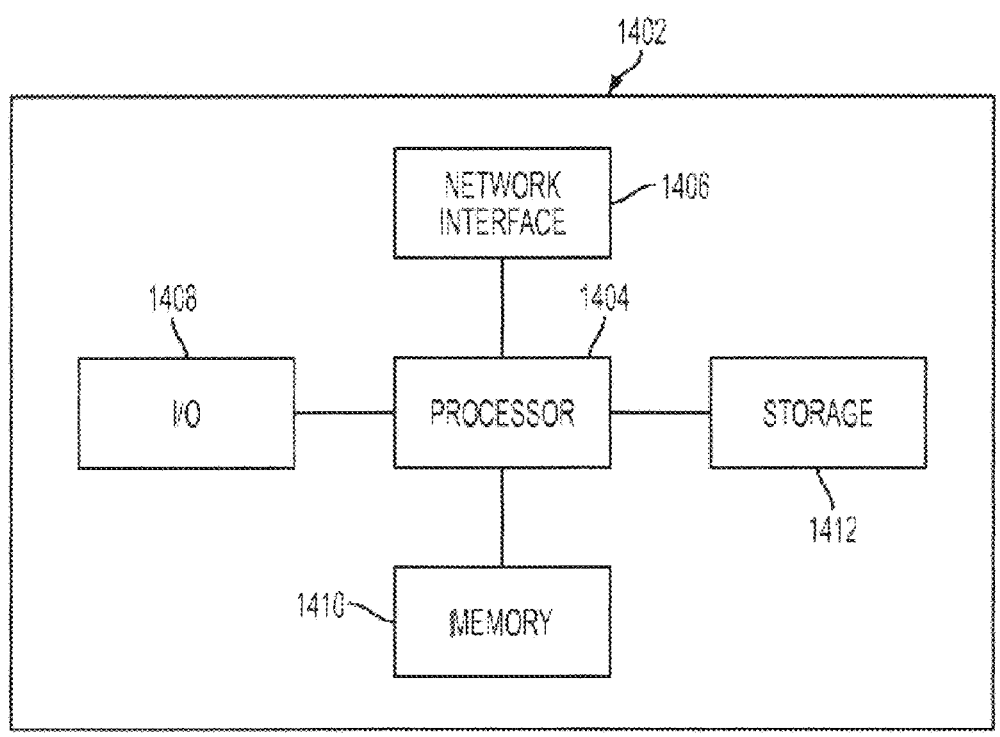
FIG. 21 depicts a high level block diagram of a computer.

The above-described methods may be implemented on a computer using well-known computer processors, memory units, storage devices, computer software, and other components. A high level block diagram of such a computer is illustrated in FIG. 21. Computer 1402 includes a processor 1404 which controls the overall operation of the computer 1402 by executing computer program instructions which define such operation. The computer program instructions may be stored in a storage device 1412, or other computer readable medium, (e.g., magnetic disk) and loaded into memory 1410 when execution of the computer program instructions is desired. Thus, all method steps described above may be defined by the computer program instructions stored in the memory 1410 and/or storage 1412 and controlled by the processor 1404 executing the computer program instructions. The computer 1402 also includes one or more network interfaces 1406 for communicating with other devices via a network. The computer 1402 also includes other input/output devices 1408 that enable user interaction with the computer 1402 (e.g., display, keyboard, mouse, speakers, buttons, etc.). One skilled in the art will recognize that an implementation of an actual computer could contain other components as well, and that FIG. 21 is a high level representation of some of the components of such a computer for illustrative purposes.

6. CONCLUSIONS

A methodology for ultrasonic inspection data reconstruction and subsequent flaw identification, grouping and sizing is presented. A software called AutoNDE-SolidRotor is developed to implement all required components and functions of the methodology. Examples of the method and software are presented for demonstration.

In order to ease the data analysis process, a system for automatic data processing, flaw identification, flaw volumetric grouping, flaw sizing, as well as visualization is developed to streamline the entire analysis procedure. A software system known as AutoNDE-SolidRotor is developed to implement all required components and functions of the methodology. The system provides a standard operation procedure for users to perform data analysis tasks with a user friendly interface. The system enables traditionally very complex and time-consuming tasks to be done efficiently and reliably. The system includes algorithms for flaw identification, grouping, and sizing. All the required components are implemented and integrated as a software system. AutoNDE-SolidRotor system has the following features provides advanced visualization capabilities. In particular, the system maps dimensionless data from ultrasonic inspection acquisition system according to the actual geometry of the target object. This process is known as data reconstruction. With high resolution 3D volumetric images and a correct geometry setting, a flaw location can be accurately calculated. The system also provides automatic flaw identification. In particular, the system implements algorithms to identify potential flaws based on the reconstructed volumetric image. The system provides an accurate and efficient approach when compared to traditional semi-empirical flaw identification. The system also provides automatic flaw grouping by providing a method to automatically group scattered indications into a flaw cluster. The treatment of a flaw cluster in the fatigue life prediction phase is different than for a single echo indication flaw. Further, the system provides flaw sizing by integrating a flaw sizing method such as a DGS method.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A method for ultrasonic inspection of a rotor, comprising:
   providing ultrasonic data, from at least one ultrasound probe of a plurality of rotor slices to a non-destructive examination processor;
   in the non-destructive examination processor:
      providing volume reconstruction of the ultrasonic data;
      providing in-slice identification, grouping and sizing of flaw indications in the rotor based on the volume reconstruction by:
         identifying ultrasound echo intensities from ultrasound data representing an ultrasonic scanning of a slice;
         identifying hit points having identified ultrasound echo intensities within the ultrasound data that exceed a pre-defined threshold;
         grouping hit points based on pixel connectivity of each of the hit points;
         identifying in-slice flaw indicators based on the hit point grouping;
      providing inter-slice identification, grouping and sizing of flaw indications based on the in-slice flaw indicators by:
         identifying hit points having identified ultrasound echo intensities within ultrasound data from a plurality of slices that exceed a pre-defined threshold;

grouping hit points based on voxel connectivity of each of the hit points;

identifying flaw indicators based on the hit point grouping; and providing flaw location and size information based on the flaw indicators to a downstream process.

2. The method according to claim 1, wherein the ultrasonic data is obtained via a phased array ultrasound probe.

3. The method according to claim 1, wherein a predefined threshold is used to locate data points in the volume reconstruction.

4. The method according to claim 3, wherein portions of the volume reconstruction having an intensity greater than the predefined threshold are each identified as hit points.

5. The method according to claim 3, further including identifying regions of interest in the volume reconstruction.

6. The method according to claim 3, wherein the predefined threshold is approximately 40%.

7. A method for ultrasonic inspection of a rotor, comprising:

scanning slices of a rotor to provide ultrasonic data, wherein the slices are perpendicular to a rotor axis and storing the ultrasonic data in a digital file;

in a non-destructive examination processor:

receiving the digital file containing the ultrasonic data;

providing volume reconstruction of the ultrasonic data;

providing in-slice identification, grouping and sizing of flaw indications in the rotor based on the volume reconstruction by:

identifying ultrasound echo intensities from ultrasound data representing an ultrasonic scanning of a slice;

identifying hit points having identified ultrasound echo intensities within the ultrasound data that exceed a pre-defined threshold;

grouping hit points based on pixel connectivity of each of the hit points;

identifying in-slice flaw indicators based on the hit point grouping;

providing inter-slice identification, grouping and sizing of flaw indications based on the in-slice flaw indicators by:

identifying hit points having identified ultrasound echo intensities within ultrasound data from a plurality of slices that exceed a pre-defined threshold;

grouping hit points based on voxel connectivity of each of the hit points;

identifying flaw indicators based on the hit point grouping; and providing flaw location and size information based on the identified flaw indicators to a downstream process.

8. The method according to claim 7, wherein a predefined threshold is used to locate data points in the volume reconstruction.

9. The method according to claim 8, wherein portions of the volume reconstruction having an intensity greater than the predefined threshold are each identified as hit points.

10. A computer readable medium encoded with computer executable instructions for performing a method for ultrasonic inspection of a rotor, the computer executable instructions defining steps that when performed by a non-destructive examination processor, cause the non-destructive examination processor to perform steps comprising:

providing ultrasonic data of a plurality of rotor slices;

providing volume reconstruction of the ultrasonic data;

providing in-slice identification, grouping and sizing of flaw indications in the rotor based on the volume reconstruction by:

identifying ultrasound echo intensities from ultrasound data in a data file representing an ultrasonic scanning of a slice;

identifying hit points having identified ultrasound echo intensities within the ultrasound data that exceed a pre-defined threshold;

grouping hit points based on pixel connectivity of each of the hit points;

identifying in-slice flaw indicators based on the hit point grouping;

providing inter-slice identification, grouping and sizing of flaw indications based on the in-slice flaw indicators by:

identifying hit points having identified ultrasound echo intensities within ultrasound data from a plurality of slices that exceed a pre-defined threshold;

grouping hit points based on voxel connectivity of each of the hit points;

identifying flaw indicators based on the hit point grouping; and providing flaw location and size information based on the identified flaw indicators to a downstream process.

* * * * *